United States Patent [19]

Caillouette

[11] Patent Number: 5,246,011
[45] Date of Patent: Sep. 21, 1993

[54] FINE NEEDLE ASPIRATION SYRINGE

[76] Inventor: James C. Caillouette, 685 Oak Knoll Cir., Pasadena, Calif. 91105

[21] Appl. No.: 827,996

[22] Filed: Jan. 30, 1992

[51] Int. Cl.⁵ .............................................. A61B 10/00
[52] U.S. Cl. .................... 128/753; 128/765; 604/187; 604/209; 604/220
[58] Field of Search ............. 604/187, 218, 208, 209, 604/220, 224, 225, 111, 239; 128/749, 752, 753, 758, 763, 765, 766

[56] References Cited

U.S. PATENT DOCUMENTS

| | | | |
|---|---|---|---|
| 1,520,795 | 12/1924 | Barr | 604/236 X |
| 2,523,850 | 9/1950 | Steinberg | 604/209 |
| 3,343,541 | 9/1967 | Bellamy | 604/111 |
| 3,727,602 | 4/1973 | Hyden et al. | |
| 3,938,505 | 2/1976 | Jamshidi | 128/753 |
| 4,266,687 | 5/1981 | Cummings | 220/257 |
| 4,370,987 | 2/1983 | Bazell et al. | 128/760 |
| 4,405,308 | 9/1983 | Jessup | 604/200 |
| 4,524,749 | 9/1985 | Caselgrandi et al. | 128/752 |
| 4,549,554 | 10/1985 | Markham | 128/753 |
| 4,552,155 | 11/1985 | Etherington et al. | 128/766 |
| 4,619,272 | 10/1986 | Zambelli | 128/753 |
| 4,643,196 | 2/1987 | Tanaka et al. | 128/753 |
| 4,817,631 | 4/1989 | Schnepp-Pesch et al. | 128/753 |
| 4,925,449 | 5/1990 | Saez et al. | 604/226 |
| 4,967,762 | 11/1990 | DeVries | 128/753 |
| 4,986,278 | 1/1991 | Ravid et al. | 128/753 |

FOREIGN PATENT DOCUMENTS 1380654 4/1964 France .................... 128/765

*Primary Examiner*—C. Fred Rosenbaum
*Assistant Examiner*—Mark O. Polutta
*Attorney, Agent, or Firm*—Christie, Parker & Hale

[57] ABSTRACT

A control syringe is provided for fine needle aspiration of biopsy tissue. An aperture through the barrel of the syringe is temporarily covered with a flexible impervious pressure sensitive adhesive tape. A low pressure created in the barrel by withdrawing the plunger is broken by peeling the tape from the barrel. Thereafter, the tape may be replaced over the aperture so that collected tissue may be discharged by moving the plunger forward. A ratchet and pawl arrangement on the syringe holds the plunger in its rearward position until released. One ratchet and pawl comprises a plurality of ratchet teeth along at least one rib of an X-shaped cross section of the plunger and a pawl on the rearward end of the barrel for engaging the ratchet teeth. Such a ratchet is released by rotating the plunger.

13 Claims, 2 Drawing Sheets

FINE NEEDLE ASPIRATION SYRINGE

BACKGROUND OF THE INVENTION

This invention relates to a syringe for drawing and releasing a vacuum so that the syringe may be used for obtaining a sample of tissue for a biopsy.

A technique which is useful for obtaining tissue samples for a biopsy is known as fine needle aspiration. When a physician suspects tissue observed by x-ray, ultrasound, or palpation may be cancerous, it is usually desirable to obtain a sample of the tissue for microscopic examination. The fine needle aspiration technique is used, for example, for sampling what appear to be lung lesions, lumps in the breast, dense prostrate tissue, or other anomalous portions of body organs.

A hollow needle or cannula is inserted, typically through the skin, so that the tip of the needle is in the suspect tissue. The plunger of the syringe is then withdrawn to pull a small amount of tissue into the hollow needle. The needle is withdrawn and the tissue sample discharged onto a slide for examination. Such aspiration of tissue into the needle may be performed in several locations in suspected tissue with a single insertion of the needle into the body.

In a typical examination using fine needle aspiration, the physician may palpate a breast to isolate and grasp a lump with one hand, and with the other hand guide the needle of an aspiration syringe into the lump. A "control" syringe may be used with finger grips on the barrel and plunger of the syringe so as to draw a vacuum in the barrel once the needle is in the lump.

At that point it becomes desirable to release the vacuum in the syringe. Failure to do so when the needle is withdrawn from the body may result in the tissue being drawn through the needle into the barrel of the syringe, where it may be lost and unavailable for biopsy. The vacuum in the barrel should not be released by simply pressing the plunger forward again since this could prematurely discharge the tissue from the needle, even before it is withdrawn from the body.

It is also desirable to introduce air into the syringe so that when the plunger is returned toward the end of the syringe, pressure in the barrel discharges tissue onto a slide for microscopic examination. It is also important for some fine needle aspiration procedures that the physician be able to operate the device entirely with one hand, at least until a sample is obtained, so that the other hand may be used to know or hold the position of the lump. Obtaining a sample of breast tissue is a good example. Breast cancer is of increasing concern for women. Improved methods for diagnosis are essential.

BRIEF SUMMARY OF THE INVENTION

There is, therefore, provided in practice of this invention according to a presently preferred embodiment, a fine needle aspiration syringe comprising a barrel and a plunger sealed in the barrel for drawing a vacuum in the barrel when the plunger is withdrawn toward a rearward position. An aperture in a side of the barrel permits air flow into the barrel for breaking a vacuum. An impervious flexible tape is temporarily adhesively attached over the aperture with at least one end of the tape free of attachment to the barrel so that it can be gripped by the fingers and peeled off of the barrel for opening the aperture.

Preferably the syringe also includes a pawl mounted on the barrel and biased toward the plunger, and a ratchet on the plunger for engaging the pawl. This permits easy withdrawal of the plunger for creating a vacuum and inhibits return of the plunger so that the vacuum can be temporarily held.

Means are also provided for releasing the ratchet and pawl for returning the plunger. A stylet may be fastened to an end of the plunger for plugging a hollow needle on the syringe when the plunger is in its forward position for excluding tissue from the hollow needle during its insertion into tissue.

BRIEF DESCRIPTION OF THE DRAWINGS

These and other features and advantages of the present invention will be appreciated as the same becomes better understood by reference to the following detailed description when considered in connection with the accompanying drawings wherein.

DETAILED DESCRIPTION

Figure 1:
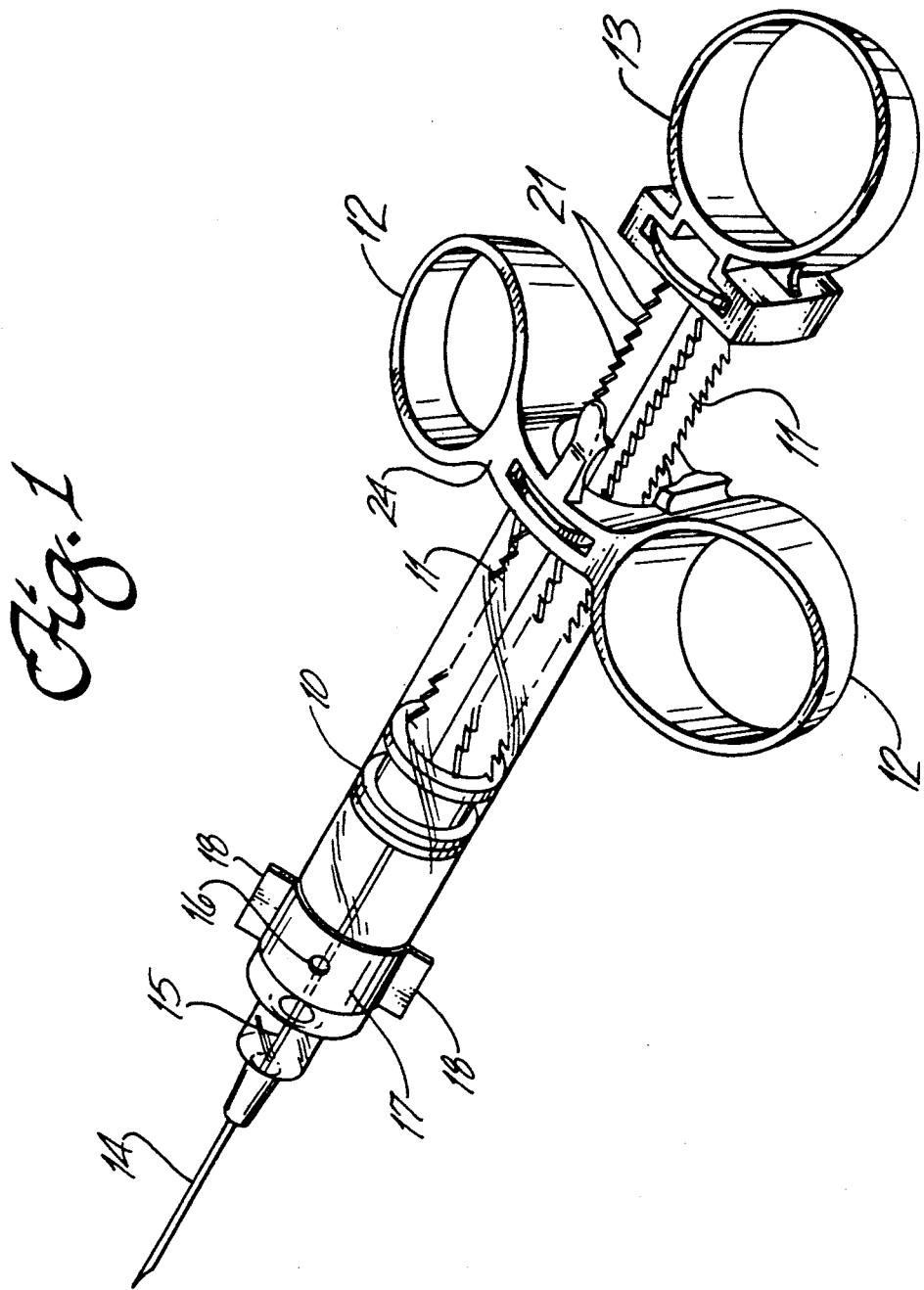
FIG. 1 illustrates isometrically a fine needle aspiration syringe constructed according to principles of this invention.
Figure 2:
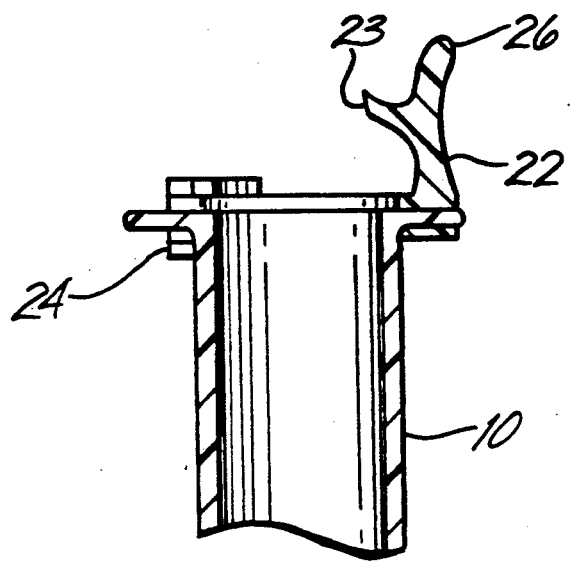
FIG. 2 illustrates in fragmentary longitudinal cross-section a ratchet and pawl arrangement for permitting withdrawal and inhibiting return of the syringe plunger.

An aspiration syringe comprises a cylindrical barrel 10 with a movable plunger 11 one end of which is sealed in the barrel, typically by an O-ring or the like so that as the plunger slides along the barrel, no fluid can pass the seal. Typically a so-called control syringe is used which has finger grips 12 secured to the barrel and a thumb ring 13 on the end of the plunger. The person operating the syringe places the fore finger and middle finger in the finger grips on the barrel, and the thumb in the ring on the plunger so that operator has good control of the syringe position and the plunger can be moved in the barrel in either direction with one hand.

A hollow needle or cannula 14 is mounted on the forward end of the barrel in a conventional manner. If desired, a solid stylet 15 having a diameter only slightly smaller than the internal diameter of the cannula is mounted on the forward end of the plunger. Thus, when the plunger is in its forward position, the stylet extends most of the way through the hollow needle and plugs it. The stylet is withdrawn from the needle when the plunger is withdrawn toward a rearward position in the barrel.

An aperture 16 is provided through the side wall of the barrel near its forward end. A narrow strip of impermeable flexible tape 17 is wrapped part way around the barrel with a central portion of the tape overlapping and sealing the aperture. The tape is temporarily adhesively attached to the barrel by a conventional reusable pressure sensitive adhesive. At each end of the tape there is a short tab 18 which is not adhesively bonded to the barrel.

When the syringe is used, the needle is inserted into the patient's body until the tip is in tissue to be sampled. The plunger is then withdrawn toward a rearward position in the barrel, thereby creating a lowered pressure in the forward end of the syringe. A stroke of 6 to 8 ml. on a 10 ml. syringe is typical for a breast biopsy, for example. Withdrawing the plunger also withdraws the stylet (if one is used) from the needle. The low pressure in the forward end of the syringe draws tissue into the needle. If desired, the needle can be probed into different portions of the tissue to acquire samples from various locations. Up to this time, the syringe can be operated with one hand while the other hand is used for palpation of the tissue or holding the mass in place.

When an adequate sample has been obtained, the person's second hand may be used to lift one of the tabs at the end of the tape and peel the tape away from the barrel, thereby exposing the aperture in the wall of the barrel and releasing the vacuum within the barrel. The needle can then be withdrawn from the tissue with a sample in the needle.

The tape is replaced over the aperture either before or after the needle is withdrawn. With the aperture thus closed, the plunger can be pressed to its forward position to discharge the tissue sample onto a slide. The impermeable adhesive tape over the aperture forms an inexpensive and readily manipulated substitute for more complex barrel venting arrangements previously proposed. Since the forward position of the plunger is forward of the aperture, it may not be important to close the aperture with the tape. The plunger can be moved forward and air vents through the aperture until the end of the plunger passes, and thereafter the air passes through the hollow needle, discharging tissue from the needle.

It is often desirable that the vacuum be maintained in the forward end of the syringe for a time. If the operator releases the plunger it could be pressed forward by external air pressure, thereby losing the vacuum and prematurely discharging the tissue sample. Means are therefore provided for inhibiting return of the plunger toward the forward position until desired.

One means for doing this comprises a plurality of ratchet teeth 21 along a portion of the length of the plunger. Most of the disposable plastic syringes in use today have a plunger with an X-shaped cross section. Ratchet teeth are molded along the length of each of the four ribs of the X-shaped cross section. A tab 22 on the end of the barrel has an inwardly directed tip 23 which acts as a pawl against the ratchet teeth. The tab is molded on the plastic member 24 which includes the finger grips 12. (Typically, the finger grips of a control syringe are formed on a separate part which clips onto the barrel of the syringe and is spot welded in place.) The tab extends beyond the end of the barrel in such a way that the tip or pawl 23 has a radial position inwardly of the maximum extent of the ribs on the plunger so that the pawl is resiliently biased toward the ratchet teeth.

When the plunger is withdrawn for creating a low pressure within the syringe, the ratchet teeth move past the pawl. When the plunger is released, the ratchet teeth prevent air pressure from pushing it forward in the barrel. When it is desired to move the plunger forward, all that is needed is to rotate the plunger up to 45° so that the pawl is between the ribs and out of engagement with the ratchet teeth. The plunger can then move forward freely. It is easy to rotate the plunger of a control syringe as much as 45° or more by simply moving the thumb from side to side, thereby engaging or releasing the ratchet. This can be done with one hand without releasing the syringe.

Alternatively, the ratchet on the plunger may be released by bending the plastic tab 22 away from the plunger. An additional extension 26 on the tab can be pressed with a person's finger to pull the tip away from the ratchet teeth and permit the plunger to return toward its forward position.

Figure 3:
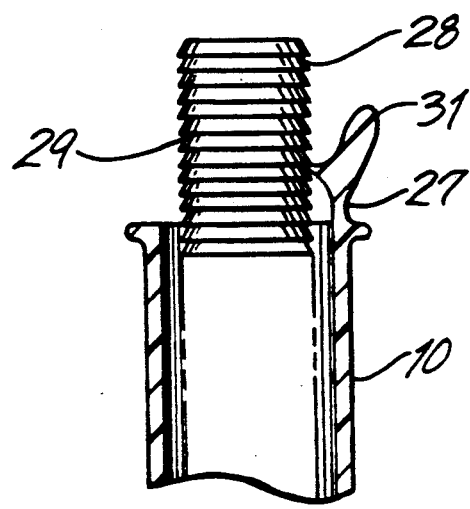
FIG. 3 illustrates in fragmentary longitudinal cross-section another embodiment of ratchet and pawl.

In another embodiment illustrated in fragmentary transverse cross section in FIG. 3, a tab 27 is formed integrally with the barrel of the syringe. The tab extends beyond the end of the barrel and inwardly for engaging ratchet teeth 28 on a plunger 29. Such an embodiment may be useful in a syringe where shallow finger grips are formed on the exterior of the barrel by a pair of laterally extending flanges. In the illustrated embodiment the ratchet teeth are formed around a cylindrical plunger. The tab also includes an extension 31 by which the operator may elastically bend the tab for releasing the tab from the teeth.

If desired, the ratchet teeth on the plunger may extend circumferentially only part way around the plunger, leaving the opposite side of the plunger smooth (not shown). Thus, the ratchet may be engaged by having the plunger in one rotational position and released by rotating the plunger 180° or less.

Although limited embodiments of fine needle aspiration syringe have been described and illustrated herein, many modifications and variations will be apparent to those skilled in the art. For example, one type of conventional syringe employs a plunger having an X-shaped cross-section. The barrel has an inwardly extending flange at the rearward end with an inner surface in the form of two to four spirally extending sectors. When the plunger is rotated, the spirally extending surfaces in the end of the barrel bite into the edges of the plunger cross-section and prevent movement of the plunger in the barrel. The plunger is released by rotating it in the opposite direction. Such an arrangement may be used in lieu of the ratchet and pawl arrangement described. Many other changes are clearly possible and it is therefore to be understood that within the scope of the appended claims, the invention may be practiced otherwise than as specifically described.

What is claimed is:

1. A fine needle aspiration syringe comprising:
   a syringe barrel;
   a plunger having an end sealed in the barrel for drawing a vacuum in the barrel when the plunger is withdrawn; means for permitting withdrawal of the plunger and inhibiting return of the plunger comprising:
      a pawl mounted on the barrel at its rearward end; and
      a ratchet on the plunger for engaging the pawl;
   an aperture in a side of the barrel; and
   an imperious flexible tape temporarily adhesively attached to the outside of the barrel having a central portion overlapping the aperture and having at least one end portion which is not adhesively attached to the barrel.

2. A fine needle aspiration syringe as recited in claim 1 further comprising means for releasing the ratchet and pawl and permitting return of the plunger.

3. A fine needle aspiration syringe as recited in claim 1 wherein the plunger has an X-shaped cross section forming ribs and the means for permitting and inhibiting comprises:
   a plurality of ratchet teeth along at least one of the ribs forming the X-shaped cross section of the plunger; and
   a pawl on the barrel for engaging the ratchet teeth.

4. A fine needle aspiration syringe as recited in claim 1 wherein the barrel comprises finger grips on opposite sides and the plunger comprises a finger grip on the end for withdrawing the plunger with one hand.

5. A fine needle aspiration syringe as recited in claim 1 wherein the tape is adhesively attached to the barrel with reusable pressure sensitive adhesive.

6. A fine needle aspiration syringe as recited in claim 5 further comprising a tab at each end of the tape which is free from the barrel for gripping with fingers for peeling the tape from the barrel.

7. A fine needle aspiration syringe as recited in claim 1 further comprising a tab at each end of the tape which is free from the barrel for gripping with fingers for peeling the tape from the barrel.

8. A fine needle aspiration syringe as recited in claim 1 further comprising;
   a hollow needle on the end of the syringe; and
   a stylet mounted on the plunger extending into the needle for plugging the needle when the plunger is forward in the barrel and clearing the needle when the plunger is withdrawn toward a rearward part of the barrel.

9. A fine needle aspiration syringe comprising:
   a hollow syringe barrel;
   a hollow needle secured on the forward end of the barrel;
   an aperture through a wall of the barrel for passage of air;
   a plunger in the barrel for translation between a forward position nearer the needle and a rearward position rearward from the aperture;
   removable means outside of the barrel for temporarily closing the aperture and preventing passage of air regardless of plunger position; and
   means for permitting withdrawal of the plunger and inhibiting return of the plunger comprising:
   a plunger with an X-shaped cross section forming ribs;
   a plurality of ratchet teeth along at least one of the ribs forming the X-shaped cross section; and
   a pawl on the barrel for engaging the ratchet teeth.

10. A fine needle aspiration syringe as recited in claim 9 wherein the removable means comprises an impervious flexible tape adhesively attached to the outside of the barrel by reusable pressure sensitive adhesive, the tape having a central portion overlapping the aperture and a tab at each end of the tape which is free from the barrel for gripping with fingers for peeling the tape from the barrel.

11. A fine needle aspiration syringe as recited in claim 9 wherein the means for permitting and inhibiting comprises:
   a pawl mounted on the barrel, including means for biasing the pawl toward the plunger;
   a ratchet on the plunger for engaging the pawl for permitting withdrawal of the plunger and inhibiting return of the plunger; and
   means for releasing the ratchet and pawl and permitting return of the plunger.

12. A fine needle aspiration syringe comprising:
   a syringe barrel;
   finger grips on the barrel for holding the barrel;
   a plunger having an end sealed in the barrel and a finger grip on the opposite end for drawing a lowered pressure in the barrel when the plunger is withdrawn;
   a pawl mounted on the barrel;
   a ratchet on the plunger for engaging the pawl for permitting withdrawal of the plunger and inhibiting return of the plunger;
   means for releasing the ratchet and pawl and permitting return of the plunger;
   an aperture in a side of the barrel;
   an imperious flexible tape temporarily adhesively attached to the outside of the barrel by reusable pressure sensitive adhesive and having a central portion overlapping the aperture; and
   a tab on at least one end of the tape which is free from the barrel for gripping with fingers for peeling the tape from the barrel.

13. A fine needle aspiration syringe as recited in claim 12 wherein the plunger has an X-shaped cross section forming ribs and further comprising:
   a plurality of ratchet teeth along at least one of the ribs forming the X-shaped cross section of the plunger; and
   a pawl on the barrel for engaging the ratchet teeth.

* * * * *